(12) United States Patent
Vagos

(10) Patent No.: US 9,995,689 B2
(45) Date of Patent: Jun. 12, 2018

(54) OPTICAL METROLOGY USING DIFFERENTIAL FITTING

(71) Applicant: Nanometrics Incorporated, Milpitas, CA (US)

(72) Inventor: Pedro Vagos, Chennevieres (FR)

(73) Assignee: Nanometrics Incorporated, Milpitas, CA (US)

( * ) Notice: Subject to any disclaimer, the term of this patent is extended or adjusted under 35 U.S.C. 154(b) by 397 days.

(21) Appl. No.: 14/720,644

(22) Filed: May 22, 2015

(65) Prior Publication Data

US 2016/0341670 A1 Nov. 24, 2016

(51) Int. Cl.
*G01N 21/55* (2014.01)
*G01N 21/88* (2006.01)
*G01N 21/21* (2006.01)
*G03F 7/20* (2006.01)

(52) U.S. Cl.
CPC ....... *G01N 21/8851* (2013.01); *G01N 21/211* (2013.01); *G01N 21/55* (2013.01); *G03F 7/70625* (2013.01); *G01N 2021/213* (2013.01); *G01N 2021/8896* (2013.01)

(58) Field of Classification Search
None
See application file for complete search history.

(56) References Cited

U.S. PATENT DOCUMENTS 6,429,930 B1 * 8/2002 Littau ................. G03F 7/70591
356/124
7,317,531 B2 * 1/2008 Mieher ................ G01N 21/956
356/369
7,446,888 B2 11/2008 Stanke et al.
(Continued)

FOREIGN PATENT DOCUMENTS

TW 201502461 A 1/2015
WO WO 2014/016056 A1 1/2014

OTHER PUBLICATIONS

International Search Report and Written Opinion, PCT/US2016/033243, International Searching Authority, dated Oct. 28, 2016, pp. 1-10.

*Primary Examiner* — Michael Lebentritt
(74) *Attorney, Agent, or Firm* — Silicon Valley Patent Group LLP

(57) ABSTRACT

Parameters of a sample are measured using a model-based approach that utilizes the difference between experimental spectra acquired from the sample and experimental anchor spectra acquired from one or more reference samples at the same optical metrology tool. Anchor parameters of the one or more reference samples are determined using one or more reference optical metrology tools. The anchor spectrum is obtained and the target spectrum for the sample is acquired using the optical metrology tool. A differential experimental spectrum is generated based on a difference between the target spectrum and the anchor spectrum. The parameters for the sample are determined using the differential experimental spectrum and the anchor parameters, e.g., by comparing the differential experimental spectrum to a differential simulated spectrum, which is based on a difference between spectra simulated using a model having the parameters and a spectrum simulated using a model having the anchor parameters.

22 Claims, 1 Drawing Sheet

(56) References Cited

U.S. PATENT DOCUMENTS

| | | | |
|---|---|---|---|
| 7,532,317 B2* | 5/2009 | Smith | G01B 11/24 356/237.2 |
| 7,561,282 B1* | 7/2009 | Widmann | G03F 7/70625 356/401 |
| 7,710,565 B2* | 5/2010 | Kaushal | G01B 21/045 356/392 |
| 7,804,994 B2 | 8/2010 | Adel et al. | |
| 8,054,467 B2* | 11/2011 | Den Boef | G03F 7/70341 356/456 |
| 8,214,771 B2* | 7/2012 | Adel | G03F 7/705 356/625 |
| 8,289,527 B2* | 10/2012 | Li | G01B 11/24 356/364 |
| 8,666,703 B2* | 3/2014 | Ferns | G03F 7/70625 700/108 |
| 9,255,877 B2* | 2/2016 | Veldman | G01N 21/211 |
| 2004/0190008 A1* | 9/2004 | Mieher | G01N 21/956 356/625 |
| 2004/0223137 A1* | 11/2004 | Littau | G03F 7/70491 356/123 |
| 2004/0267397 A1* | 12/2004 | Doddi | G01B 11/24 700/110 |
| 2007/0215801 A1* | 9/2007 | Walsh | G01B 11/0625 250/252.1 |
| 2007/0220458 A1 | 9/2007 | Zhou et al. | |
| 2007/0268498 A1 | 11/2007 | Stanke et al. | |
| 2011/0245955 A1* | 10/2011 | Li | G01B 11/24 700/104 |
| 2011/0246141 A1* | 10/2011 | Li | G01B 21/24 703/2 |
| 2012/0226644 A1* | 9/2012 | Jin | G06N 3/08 706/19 |
| 2013/0325395 A1* | 12/2013 | Zhou | G01B 11/02 702/155 |
| 2014/0249768 A1* | 9/2014 | Vagos | G06F 17/00 702/104 |
| 2016/0097677 A1* | 4/2016 | Shachaf | G01J 3/28 702/189 |
| 2016/0196379 A1* | 7/2016 | Adel | G03F 1/36 716/52 |
| 2016/0246285 A1* | 8/2016 | Veldman | G01B 11/0641 |
| 2016/0313658 A1* | 10/2016 | Marciano | G03F 9/7003 |

* cited by examiner

OPTICAL METROLOGY USING DIFFERENTIAL FITTING

BACKGROUND

Background Field

Embodiments of the subject matter described herein are related generally to optical metrology, and more particularly to optical metrology using a model based approach.

Relevant Background

Semiconductor and other similar industries, often use optical metrology equipment to provide non-contact evaluation of substrates during processing. Optical metrology techniques, such as ellipsometry and reflectometry, typically operate by illuminating a sample with a probe beam of electromagnetic radiation and then detecting and analyzing the reflected and/or transmitted energy. The probe beam may be polarized or unpolarized radiation, and may include one or more wavelengths of radiation. Ellipsometry typically measures changes in the polarization state of the reflected beam after interacting with the sample, while reflectometry measures changes in the magnitude of the reflected beam.

One type of optical metrology utilizes a model based approach to determining parameters of interest in a sample under test. For example, spectroscopic optical critical dimension (OCD) determines parameters such as critical dimension (CD), sidewall angle (SWA) and thicknesses of features of a target by fitting spectra simulated using a model to experimental spectra from the sample under test. The fitting process may use a cost function in which the model parameters, i.e., the CD's, SWA's, thicknesses, etc, are varied until a best fit is obtained or a library may be used.

It is desirable to remove sources of error in optical metrology techniques to reduce or eliminated contributors of the total measurement uncertainty (TMU).

SUMMARY

Parameters of a sample are measured using a model-based approach that utilizes the difference between experimental spectra acquired from the sample and experimental anchor spectra acquired from one or more reference samples at the same optical metrology tool. Anchor parameters of the one or more reference samples are determined using one or more reference optical metrology tools. The anchor spectrum is obtained and the target spectrum for the sample is acquired using the optical metrology tool. A differential experimental spectrum is generated based on a difference between the target spectrum and the anchor spectrum. The parameters for the sample are determined using the differential experimental spectrum and the anchor parameters, e.g., by comparing the differential experimental spectrum to a differential simulated spectrum, which is based on a difference between spectra simulated using a model having the parameters and a spectrum simulated using a model having the anchor parameters.

In one implementation, a method of measuring parameters of a sample with an optical metrology tool includes obtaining an anchor spectrum for one or more reference samples using the optical metrology tool; acquiring a target spectrum for the sample using the optical metrology tool; generating a differential experimental spectrum based on a difference between the target spectrum and the anchor spectrum; and determining the parameters for the sample based on a comparison of the differential experimental spectrum to a differential simulated spectrum, wherein the differential simulated spectrum is based on a difference between a spectrum simulated using a model having the parameters and a spectrum simulated using a model having anchor parameters, wherein the anchor parameters are obtained from one or more reference samples and are determined using one or more reference optical metrology tools.

In one implementation, an optical metrology tool includes an illumination source to produce illumination; an optical system that focuses the illumination into incident light on a sample; a detector that detects the illumination after being incident on the sample; and a processor coupled to receive an output signal from the detector, wherein the processor is configured to acquire an anchor spectrum for one or more reference samples, wherein the anchor spectrum is acquired using the optical metrology tool, acquire a target spectrum for the sample from the output signal from the detector, generate a differential experimental spectrum based on a difference between the target spectrum and the anchor spectrum, and determine the parameters for the sample based on a comparison of the differential experimental spectrum to a differential simulated spectrum, wherein the differential simulated spectrum is based on a difference between a spectrum simulated using a model having the parameters and a spectrum simulated using a model having anchor parameters, wherein the anchor parameters are obtained from one or more reference samples and are determined using one or more reference optical metrology tools.

BRIEF DESCRIPTION OF THE DRAWINGS

FIG. 2 illustrates a model of a target from a Hard Mask Gate application.

FIG. 3 illustrates graphs showing best fit ellipsometric NCS spectra for the target shown in FIG. 2 and the corresponding residual spectra.

FIG. 4 illustrates a fleet of optical metrology tools that may be used with the differential fitting process described herein.

FIG. 5 is a flow chart illustrating a method of measuring parameters of a sample with an optical metrology tool using differential fitting.

FIGS. 6A, 6B, and 6C schematically illustrate measuring parameters of a sample using differential fitting.

FIG. 7 illustrates a model of a target from an NFET application.

FIG. 8 illustrates a number of plots showing the measured sample spectra, model bias, tool-to-tool mismatch, and experimental differential spectra from the measurement of the target shown in FIG. 7.

FIG. 9 illustrates the average parameter mismatch between two optical metrology tools measuring two different wafers using a conventional fitting approach and the differential fitting approach described herein.

DETAILED DESCRIPTION

Figure 1A:
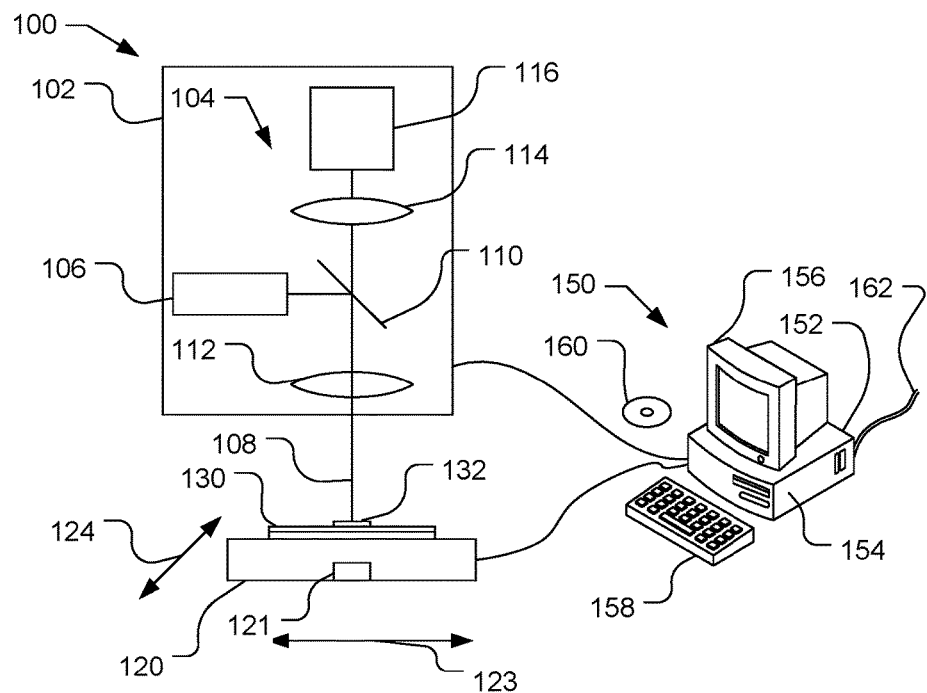
FIGS. 1A and 1B illustrate optical metrology tools that may be used with the differential fitting process described herein.

FIG. 1A shows a schematic view of an optical metrology device 100, including an optical head 102 coupled to a computer 150, such as a workstation, a personal computer, central processing unit or other adequate computer system, or multiple systems, that performs spectroscopic optical critical dimension (OCD) metrology in accordance with one or more embodiments as described herein. The optical metrology device 100 illustrated in FIG. 1A is, e.g., a spectroscopic reflectometer. If desired, multiple optical heads, i.e., different metrology devices, may be combined in the same metrology device 100. The computer 150 may also control the movement of a stage 120 that holds the sample 130 via actuators 121 and/or the optical head 102. The stage 120 may be capable of horizontal motion in either Cartesian (i.e., X and Y) coordinates, as indicated by arrows 123 and 124, or Polar (i.e., R and θ) coordinates or some combination of the two. The stage 120 and/or optical head 102 may also be capable of vertical motion, e.g., for focusing.

The optical head 102 may include an optical system 104 including a broadband light source 106, such as a Xenon Arc lamp and/or a Deuterium lamp, and a detector 116, such as a spectrometer. In operation, light produced by the light source 106 may be directed along an optical axis 108, e.g., via beam splitter 110, toward the sample 130 which includes a target 132. An objective 112 focuses the light onto the target 132 and receives light that is reflected from the target 132. The reflective light may pass through the beam splitter 110 and is focused with lens 114 onto the detector 116. The detector 116 provides a spectroscopic signal to the computer 150. The objective 112, beam splitter 110, lens 114, and detector 116 are merely illustrative of typical optical elements that may be used. Additional optical elements, such as a polarizer and/or analyzer, may be used if desired. Moreover, generally, additional optical elements such as field stops, lenses, etc. may be present in the optical system 104.

The computer 150 includes a processor 152 with memory 154, as well as a user interface including e.g., a display 156 and input devices 158. The anchor spectra obtained by the optical metrology device 100 using one or more reference samples, as discussed herein, may be may be stored at least temporarily in memory 154 or in non-transitory computer-usable storage medium 160. Additionally, as discussed herein, the anchor parameters for the one or more reference samples obtained by one or more reference optical metrology devices, or a simulated spectrum produced using a model having the anchor parameters, or a library of differential simulated spectrum based on a difference between spectra simulated using a model having floating parameters and the spectrum simulated using a model having the anchor parameters, may be stored at least temporarily in memory 154 or in non-transitory computer-usable storage medium 160.

Additionally, non-transitory computer-usable storage medium 160 may have computer-readable program code embodied thereon and may be used by the computer 150 for causing the processor to control the metrology device and to perform the functions described herein. The data structures and software code for automatically implementing one or more acts described in this detailed description can be implemented by one of ordinary skill in the art in light of the present disclosure and stored, e.g., on a computer readable storage medium 160, which may be any non-transitory device or medium that can store code and/or data for use by a computer system such as processor 152. The computer-usable storage medium 160 may be, but is not limited to, magnetic and optical storage devices such as disk drives, magnetic tape, compact discs, and DVDs (digital versatile discs or digital video discs). A communication port 162 may also be used to receive instructions that are stored in memory 154 or other storage in computer 150 and used to program the computer 150 to perform any one or more of the functions described herein and may represent any type of communication connection, such as to the internet or any other computer network. Additionally, the functions described herein may be embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

Figure 1B:
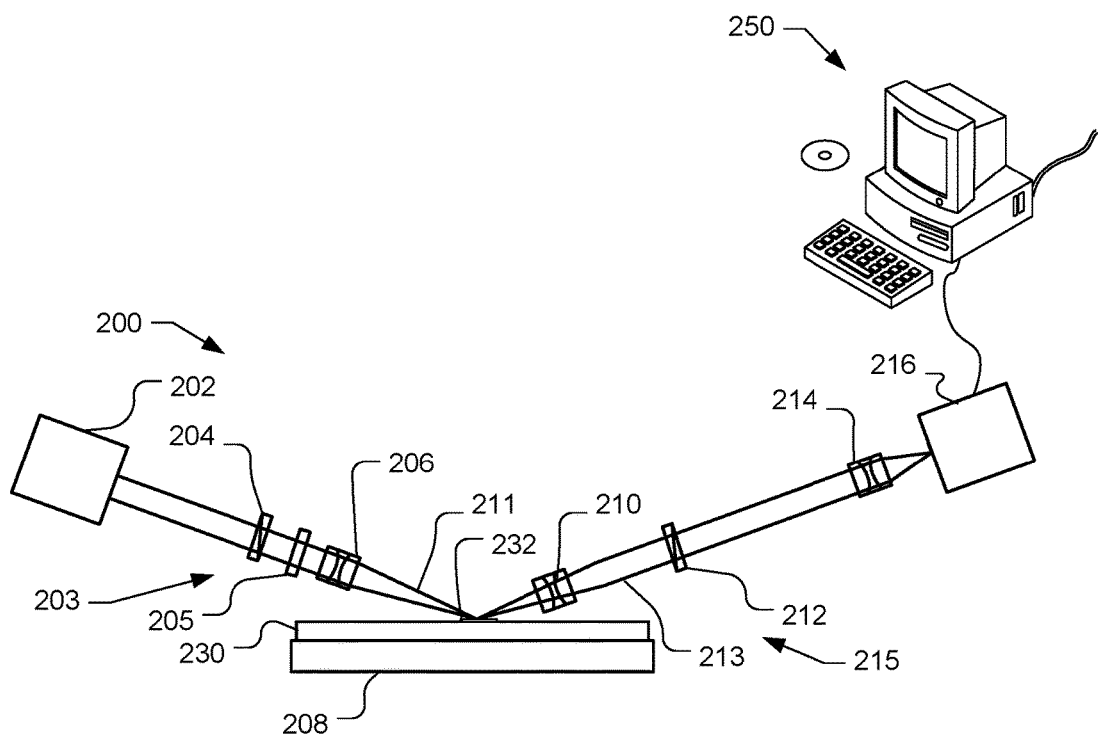

FIG. 1B shows a schematic view of another optical metrology device 200 that may perform the differential fitting process as discussed herein. Optical metrology device 200 is illustrated as a spectroscopic ellipsometer with computer 250, substantially similar to computer 150 discussed above, but configured to operate a spectroscopic ellipsometer as opposed to a spectroscopic reflectometer.

Ellipsometer 200 is illustrated as including a broadband light source 202 and a polarization state generator 203 with a polarizer 204 and a rotating compensator 205, as well as a lens system 206 that focuses the illuminating light 211 into a measurement spot on the surface of a sample 230 that is positioned on a stage 208. The incident illuminating light 211 has a known polarization state due to the polarizer 204 and rotating compensator 205. The polarization state of the light reflected by the sample 201 is analyzed by a polarization state analyzer 215, e.g., by passing the reflected light 213 through another polarizer 212, commonly referred to as analyzer 212, after passing through another lens system 210. After passing through the analyzer 212, the reflected light 213 is focused by a lens system 214 on a detector 216, which is coupled to the computer 250. In use, a sample under test will change the polarization state of the incident light, which will change the intensity and phase of the resulting signal from the detector 216. Using the change in intensity and phase, the material properties of the sample 230 may be determined, which is the essence of ellipsometry and is well known in the art.

The spectroscopic reflectometer 100 and spectroscopic ellipsometer 200 are capable of, e.g., spectroscopic OCD and TF (through focus) measurements, which are model-based measurements. It should be understood, however, that while a spectroscopic reflectometer and spectroscopic ellipsometer are specifically discussed herein, the differential fitting process discussed herein is not limited thereto. Moreover, the differential fitting process is not limited to OCD or TF types of measurements. Any type of optical metrology device or type of metrology that utilizes a model-based approach may be used with the differential fitting process.

Model-based measurement use a theoretical model of the sample under test as well as the measurement tool in order to produce a simulated spectrum, which is the spectrum expected from the actual measurement of the sample by the measurement tool, i.e., the experimental spectrum. The simulated spectrum is compared to the experimental spectrum to determine if the simulated spectrum fits the experimental spectrum. Parameters, such as film thicknesses, CD, and SWA, of the theoretical model are adjusted to produce a number of simulated spectra, which are compared to the experimental spectrum to determine the best fit. The adjustment of the parameters and production of a number of simulated spectra may be performed before testing of the sample and stored in a library. The parameters of the theoretical model that produce a simulated spectrum having the best fit to the experimental spectrum are presumed to accurately describe the sample under test.

Fitting the simulated spectra to the experimental spectrum is typically done by an optimization algorithm, for example the Levenberg-Marquardt algorithm, where the parameter values that minimize the difference between the simulated spectrum and the experimental spectrum are searched. The difference between the simulated spectrum and the experimental spectrum may be assessed by a cost function, for example, in a form such as:

$$F = \sum_{n=1}^{N} [w_n \cdot (Y_e(\lambda_n) - Y_S(\lambda_n, P))]^2 \quad \text{eq. 1}$$

where $Y_e$ and $Y_s$ are respectively the experimental spectrum and the simulated spectrum, $\lambda_n$ is the wavelength data point, P is the vector of the model parameters that are adjusted (floated), $w_n$ is a weight function and the sum is over the N data points of the spectra. The weight function $w_n$ is often equal to 1 and thus the function F is proportional to the mean square error (MSE). When the weight function $w_n$ is dependent on wavelength, certain spectral regions are emphasized to the detriments of others. For example if the weight function $w_n$ is the inverse of the spectrum noise 1 sigma ($w_n = (1/\sigma_Y)$), the less noisy regions of the spectrum are more weighted than the more noisy regions of the spectrum.

Once the best fit is obtained, e.g., at $P=P_o$, a remaining spectrum residual dY may be given by:

$$dY(\lambda_n) = Y_e(\lambda_n) - Y_S(\lambda_n, P_o) \quad \text{eq. 2}$$

If the theoretical model corresponding to the best fit were perfect, the residual dY would be the result of only tool noise. In such a case, the residual dY would be independent of wavelength, i.e., for each wavelength $\lambda_n$ the residual dY would take a random value centered at zero, and for two different wavelengths, $\lambda_1$ and $\lambda_2$, the residuals would be completely independent of each other.

In practice, however, the residual dY is not the result of only tool noise, because almost always the actual measurement tool has some small non-idealities, the real sample has some imperfections, and the model of the sample is often a simplistic physical description of the real sample (for example, for grating samples, the exact rounding of the edges is often ignored in the model). As a result, the simulated spectrum that best fits the experimental spectrum always presents a small residual dY that not only contains a random tool noise component, but also contains a component that is not random. The non-random component is, in fact, a smooth function of wavelength and is a direct consequence of the limitations of representing a real sample and tool with a theoretical model. This non-random component of the residual dY will be denoted herein as the "model bias."

By way of illustration of model bias, FIGS. 2 and 3 illustrate a target and best fit spectra for the target along with corresponding residual dY. FIG. 2 illustrates a model of a "Hard Mask Gate" (HMG) target 300 that includes a silicon substrate 302 with an oxide layer 304 and a poly-silicon layer 304, over which is an oxide grating 308. FIG. 3 illustrates graphs showing best fit ellipsometric NCS spectra for an HGM target and the corresponding residual dY, where $N=\cos(2\psi)$; $C=\sin(2\psi)\cdot\cos(\Delta)$; $S=\sin(2\psi)\cdot\sin(\Delta)$. For example, graphs 312, 314, and 316 illustrate the best fit simulated spectra $Y_s(P_o)$ with dark lines and the experimental spectra $Y_e$ with light lines. The simulated NSC spectra was produced using RCWA (rigorous coupled wave analysis) model. Graphs 313, 315, and 317 illustrate the residuals $dY = Y_e - Y_s(P_o)$, for the N, S and C spectra. As can be seen, the residual dY includes a non-random component that varies smoothly with respect to wavelength, thereby demonstrating a significant model bias.

Often the model bias is relatively large with respect to the spectral noise level, especially on complex targets. For example, the model bias is typically more than one order of magnitude larger than the spectral noise level. As a result, the fitted parameters $P_o$ may shift significantly from the true values thereby corroding the accuracy of the measured parameters (i.e. the thicknesses, CD's, SWA's, etc). Accordingly, model bias is a significant contributor of the total measurement uncertainty (TMU).

Another contributor to TMU is tool-to-tool mismatch. Often, metrology tools are deployed in a fleet. FIG. 4, by way of example, illustrates a fleet 400 that includes a plurality of metrology tools 100A, 100B, 100C, and 100D. Despite best efforts to perform a good tool calibration on each of the metrology tools in the fleet 400, the response of each metrology tool is slightly different. Thus, the same sample measured on two healthy and properly calibrated metrology tools, e.g., metrology tools 100A and 100B, will result in two slightly different spectra. The difference between these two spectra contains a noise component (typically white noise) and a tool-to-tool spectral mismatch component, which is approximately smooth with respect to wavelength. The tool-to-tool spectral mismatch is a constant component, i.e., repeat measurements will result in a different noise component but the same tool-to-tool mismatch component. As with the model bias, the spectral tool-to-tool mismatch may be relatively large with respect to the spectral noise level.

Both the tool-to-tool spectral mismatch and the model bias tend to shift the fitted parameters $P_o$ away from the true values $P_{true}$. For example in a wafer-map, the distribution of the values of $P_o$ along the X,Y coordinates of the wafer can be significantly deformed from the real distribution of $P_{true}$. Accordingly, both the model bias and tool-to-tool mismatch contribute significantly to the total measurement uncertainty (TMU).

In practice, conventionally attempts to improve the TMU due to model bias and/or tool-to-tool mismatch are difficult and time consuming. For example, improving the tool-to-tool spectral mismatch is typically performed using a "try-and-see" approach of adjusting the hardware of the metrology tools, modifying the tool-calibration parameters, replacing parts of the tool, etc. Minimizing the model bias is typically performed by including more layers of complexity in the model to improve the fitting quality. Adding layers of complexity in the model, however, requires a time investment that can grow exponentially for small incremental improvements and is often limited by the prior knowledge of the user with respect to the target. Another approach to improve the TMU uses a post-measurement recalibration based on some reference data, either from a "golden" reference tool or from another metrology technique such as Critical Dimension-Scanning Electron Microscoy (CD-SEM). The reference data may be used to find a multi-dimensional linear transform to correct the measured OCD values. This approach, however, is not well accepted by many customers.

The impact of tool-to-tool spectral mismatch and/or model bias on TMU may be minimized using a differential fitting approach. With differential fitting, the difference between spectra from two different samples is fit, as opposed to the spectrum itself. The two different samples are of the same application, i.e., samples built using the same fabrication process and nominal values, but due to the inherent fabrication variability their parameters, such as thicknesses, CD's SWA's, etc. may vary slightly. Use of the differential fitting approach may improve the tool-to-tool matching and accuracy of the measured parameters.

For purposes of illustrating the differential fitting approach, the experimental spectra from samples #1 and #2 (targets) of the same application, measured at optical metrology tool "t", will be denoted as $Y_{t1}$ and $Y_{t2}$. The spectra for the samples is simulated using a model, where the simulated spectra is denoted as $Y_s(P)$ where P is the vector of model parameters.

The conventional approach will fit the simulated spectra $Y_s(P)$ to each of the experimental spectra $Y_{t1}$ and $Y_{t2}$ by applying equation 1 and minimizing the cost function F to obtain the fitted values $P_1$ and $P_2$ for the samples #1 and #2, respectively. Thus, the fitted values of the samples #1 and #2 would conventionally be obtained successively and independently of each other.

Using the differential fitting approach, the simulated spectra $Y_s(P)$ is not successively fit to the experimental spectra $Y_{t1}$ and $Y_{t2}$, but instead a difference $\Delta Y_t$ between the experimental spectra $Y_{t1}$ and $Y_{t2}$ will be fit, where the difference $\Delta Y_t$ is defined as:

$$\Delta Y_t = (Y_{t1} - Y_{t2}) \qquad \text{eq. 3}$$

In order to make the differential fitting approach meaningful, all the measurements for a metrology tool "t", i.e. all of the fittings, will be done relative to an "anchor" spectrum obtained from one or more reference samples at the metrology tool "t", the anchor spectrum from metrology tool "t" is denoted herein as $Y_{t,anchor}$. The anchor spectrum may be referred to as a "reference spectrum," however, it should be understood that the anchor spectrum (reference spectrum) is not necessarily associated with only a single reference sample but may be obtained from more than one reference samples. A reference sample is a given target of a given wafer of the same application as the sample to be measured, i.e., the one or more reference samples are produced with the same nominal values as the sample under test. If more than one reference sample is used, the spectra from each of a plurality of reference samples is acquired at the metrology tool "t" and statistically combined, e.g., averaged, to produce the anchor spectrum. The anchor spectrum $Y_{t,anchor}$ from the one or more reference samples obtained by metrology tool "t" provides a fixed point of reference for the differential fitting approach on metrology tool "t" for every sample under test subsequently measured on metrology tool "t", and accordingly, is referred to herein as the "anchor." Thus, in equation 3, one of the experimental spectra, e.g., $Y_{t2}$ will be the anchor spectrum $Y_{t,anchor}$, to produce the differential experimental spectrum $\Delta Y_{t,1}$ for the test sample #1, as follows:

$$\Delta Y_{t,1} = (Y_{t1} - Y_{t,anchor}). \qquad \text{eq. 4}$$

Additionally, the parameters for the one or more reference samples are determined and are denoted herein as the anchor parameters "$P_{anchor}$." The anchor parameters $P_{anchor}$ may be determined by acquiring the spectra for the one or more reference samples at one or more reference tools. The anchor parameters may be referred to as "reference parameters," however, it should be understood that the anchor parameters (reference parameters) are not necessarily associated with only a single reference sample or a single reference optical metrology tool, but may be obtained from more than one reference samples measured at more than one reference optical metrology tool. For example, a single reference metrology tool, sometimes referred to as the golden metrology tool "g," may be used to acquire the spectrum for a single reference sample. A golden metrology tool "g" is a reference metrology tool that produces measurements that all other metrology tools in the fleet should match. The spectrum from the reference sample that is acquired at the golden metrology tool, denoted as $Y_{g,anchor}$, may be used to determine the anchor parameters $P_{anchor}$ in a conventional manner, e.g., by fitting the acquired experimental spectrum $Y_{g,anchor}$ to the simulated spectrum $Y_s$. If a plurality of reference samples are used, the spectra from the plurality of reference samples acquired by the golden metrology tool may be statistically combined, e.g., averaged, and used to determine the anchor parameters $P_{anchor}$ in a conventional manner, e.g., by fitting to the simulated spectrum $Y_s$. Alternatively, the parameters for each reference sample may be determined, e.g., in the conventional manner, and the parameters may be combined, e.g., averaged, to determine the anchor parameters $P_{anchor}$.

If desired, a plurality of reference metrology tools, as opposed to a single reference metrology tool, may be used to determine the anchor parameters $P_{anchor}$. For example, a number or all of the optical metrology tools in the fleet may be used as reference metrology tools to acquire the spectra from one or more reference samples. While the optical metrology tools are members of the fleet of optical metrology tools and will be subsequently, measuring samples under test, they are referred to here as "reference" optical metrology tools because they are being used to generate the anchor parameters $P_{anchor}$. The spectra acquired from the plurality of metrology tools may be statistically combined, e.g., averaged, and used to determine the anchor parameters $P_{anchor}$ in a conventional manner, e.g., by fitting the resulting combined spectrum to the simulated spectrum $Y_s$. Alternatively, parameters for each of the one or more reference samples may be acquired for the number or all of the optical metrology tools in the fleet and the parameters statistically combined, e.g., averaged, to determine the anchor parameters $P_{anchor}$.

Once the anchor parameters $P_{anchor}$ are determined, e.g., by one or more reference optical metrology tools, the anchor parameters $P_{anchor}$ may be stored, e.g., in memory 154, to be used by each metrology tool "t." Additionally, or alternatively, a spectrum for the sample may be simulated using a model with the anchor parameters, and the simulated spectrum based on the anchor parameters may be stored in memory 154 to be used by each metrology tool "t." Additionally, or alternatively, a library of differential simulated spectrum may be generated based on a difference between spectra for the sample that is simulated using a model with floating parameters and the spectrum simulated using a model having the anchor parameters, which may be stored in memory 154. In addition, the anchor spectrum $Y_{t,anchor}$ for the one or more reference samples is acquired by each separate metrology tool "t" and stored, e.g., in memory 154.

Thus, to measure an arbitrary sample "k" at a given optical metrology tool "t," anchor parameters $P_{anchor}$ are determined and saved, or spectra simulated using the anchor parameters $P_{anchor}$ are determined and saved, as discussed above. The anchor spectrum $Y_{t,anchor}$ for the one or more reference samples is also acquired at the metrology tool "t." The sample spectrum $Y_{t,k}$ from the sample "k" is acquired at the metrology tool "t." Having acquired the sample spectrum $Y_{t,k}$, the anchor spectrum $Y_{t,anchor}$, and the anchor parameters $P_{anchor}$, the differential fitting may be performed by minimizing the cost function, for example, as show in the following:

$$F = \sum_{n=1}^{N} [w_n \cdot (\Delta Y_{t,k}(\lambda_n) - \Delta Y_s(\lambda_n, P))]^2 \quad \text{eq. 5}$$

with $\Delta Y_{t,k} = Y_{t,k} - Y_{t,anchor}$ eq. 6 and $\Delta Y_s(P) = Y_s(P) - Y_s(P_{anchor})$. eq. 7

The differential experimental spectrum $\Delta Y_{t,k}$ is the difference between the experimental spectrum $Y_{t,k}$ acquired by metrology tool "t" for the sample "k" and the anchor spectrum $Y_{t,anchor}$ for the one or more reference samples acquired by the same metrology tool "t." The differential simulated spectrum $\Delta Y_s$ is the difference between the simulated spectra $Y_s$ produced by a model with the floated parameters P and with the anchor parameters $P_{anchor}$.

If desired, rather than determining the parameters for a sample under test in real-time using a cost function and varying parameters P to find a best fit, a library may be used. The library may associate the differential simulated spectra $\Delta Y_s$ with the parameters of interest. Each of the differential simulated spectra $\Delta Y_s$ is the difference between the simulated spectra $Y_s$ produced by a model with particular values of the floated parameters P and with the anchor parameters $P_{anchor}$. Each of the differential simulated spectrum $\Delta Y_s$ may be associated with differential parameters $\Delta P$, i.e., the difference between the values of the floated parameters P and the values of the anchor parameters $P_{anchor}$. Alternatively, each of the differential simulated spectrum $\Delta Y_s$ may be associated with the values of the sample parameters $P_{sample}$, where $P_{sample} = P_{anchor} + \Delta P$. Accordingly, in use, the differential experimental spectrum $\Delta Y_{t,k}$ is compared to the library to find the best matching differential simulated spectrum $\Delta Y_s$. The sample parameters may then be provided based on the parameters associated with the matching differential simulated spectrum $\Delta Y_s$. Where the library associates differential parameters $\Delta P$ with differential simulated spectra $\Delta Y_s$, once the matching differential simulated spectra $\Delta Y_s$ is found, the sample parameters $P_{sample}$ may be determined by summing the anchor parameters $P_{anchor}$ and the differential parameters $\Delta P$, i.e., $P_{sample} = P_{anchor} + \Delta P$.

FIG. 5, by way of example, is a flow chart illustrating a method of measuring parameters of a sample with an optical metrology tool using differential fitting, which may be performed by one or more optical metrology tools, such as metrology tools 100, 200 shown in FIGS. 1A and 1B, which may be included in a fleet of metrology tools. As illustrated, an anchor spectrum for the one or more reference samples is obtained using the optical metrology tool (502). Each of the one or more reference samples and a sample to be tested are associated with the same application, wherein the application defines one or more fabrication processes and process parameters. If a plurality of reference samples are used, the anchor spectrum may be produced by acquiring a spectrum for each of the reference samples using the optical metrology tool and combining the spectra to produce the anchor spectrum. A target spectrum is acquired for the sample using the optical metrology tool (504). The anchor spectrum and the target spectrum may be functions of at least one of wavelength, angle of incidence, angle of azimuth or a combination of the foregoing. For example, the angle of azimuth may be relative to a grating orientation on the target. Additionally, the anchor spectrum and the target spectrum may be one of reflectance spectra, ellipsometric spectra, Mueller matrix spectra, Jones matrix spectra or Fourier coefficients spectra.

A differential experimental spectrum is generated based on a difference between the target spectrum and the anchor spectrum (506). The parameters for the sample are determined based on a comparison of the differential experimental spectrum to a differential simulated spectrum (508). The differential simulated spectrum is based on a difference between a spectrum simulated using a model having the parameters and a spectrum simulated using a model having anchor parameters. The anchor parameters are obtained from one or more reference samples and are determined using one or more reference optical metrology tools. As discussed above, the anchor parameters for the one or more reference samples may be determined using a fitting process, e.g., by acquiring an experimental spectrum from the one or more reference samples and fitting the acquired experimental spectrum to a simulated spectrum. The anchor parameters may be a statistical combination, e.g., an average, of parameters determined for a plurality of reference samples. Alternatively, the anchor parameters may be determined using a statistical combination, e.g., an average, of spectra acquired for a plurality of reference samples. Additionally, as discussed above, the anchor parameters may be determined using a single reference optical metrology tool, e.g., a golden tool, or using a plurality of reference optical metrology tools. For example, the anchor parameters may be determined based on a statistical combination of parameters determined for one or more reference samples using a plurality of reference optical metrology tools. Alternatively, the anchor parameters may be determined using a statistical combination of spectra acquired for one or more reference samples using a plurality of reference optical metrology tools.

The comparison of the differential experimental spectrum to the differential simulated spectrum to determine the parameters may be fitting the differential experimental spectrum to the differential simulated spectrum. For example, fitting the differential experimental spectrum to the differential simulated spectrum may be performed by minimizing a cost function to determine the parameters of the sample. In another example, differential simulated spectra may be stored in a library and fitting the differential experimental spectrum to the differential simulated spectrum may be performed by determining the differential simulated spectrum is a best match in the library for the differential experimental spectrum or interpolating the differential experimental spectrum based on entries in the library.

As discussed above, the anchor parameters for the one or more reference samples may be determined using a fitting process, e.g., by acquiring an experimental spectrum from the one or more reference samples and fitting the acquired experimental spectrum to a simulated spectrum. The anchor parameters may be a statistical combination, e.g., an average, of parameters determined for a plurality of reference samples. Alternatively, the anchor parameters may be determined using a statistical combination, e.g., an average, of spectra acquired for a plurality of reference samples. Additionally, as discussed above, the anchor parameters may be determined using a single reference optical metrology tool, e.g., a golden tool, or using a plurality of reference optical metrology tools. For example, the anchor parameters may be determined based on a statistical combination of parameters determined for one or more reference samples using a plurality of reference optical metrology tools. Alternatively, the anchor parameters may be determined using a statistical combination of spectra acquired for one or more reference samples using a plurality of reference optical metrology tools.

It should be understood that while OCD and TF types of optical metrology devices have been described herein, the use of the differential fitting approach is not limited to these specific types of optical metrology. For example, the different fitting approach may be used in any field where the metrology is performed by a model-based approach, i.e. where a simulated signal is fitted to an experimental signal in order to infer the parameters of interest. Further, to the extent a cost function is used to find the parameters of interest, the cost function does not need to have the form given by equation 5. Any cost function may be used to fit a simulated signal to an experimental signal as appropriate for the specific implementation.

FIGS. 6A, 6B, and 6C illustrate measuring parameters of a sample with an optical metrology tool using differential fitting as discussed above. FIG. 6A, for example, schematically illustrates a reference optical metrology tool 600 determining anchor parameters for a reference sample (RS) 602. As discussed above, more than one reference optical metrology tool and/or more than one reference sample may be used to determine the anchor parameters. The anchor parameters may be determined, e.g., by fitting a spectrum acquired from the reference sample 602 by the reference optical metrology tool to a simulated spectrum, e.g., by minimizing a cost function as shown in equation 1.

FIG. 6B illustrates an optical metrology tool 610 acquiring an anchor spectrum for the reference sample 602. The optical metrology tool 610 is a different tool than the reference optical metrology tool 600, but may belong to the same fleet of tools as the reference optical metrology tool 600. In one implementation, if more than one reference optical metrology tool is used, the optical metrology tool 610 may be one of the reference optical metrology tools.

FIG. 6C illustrates the optical metrology tool 610 acquiring a target spectrum from a sample under test (SUT) 612. As illustrated by box 620, using the target spectrum and the anchor spectrum, e.g., to generate a differential experimental spectrum, and using the anchor parameters, the sample parameters may be determined, e.g., using a fitting process. For example, a fitting process, such as that illustrated in equation 5 may be used or a fitting process in which a best match in a library of differential simulated spectra may be used.

FIGS. 7 and 8 illustrate an example measuring parameters of a sample using differential fitting as discussed above. FIG. 7 illustrates a target 700 from an NFET application that was measured using two different optical metrology tools of the same type. FIG. 8 illustrates a number of plots showing the measured sample spectra, model bias, tool-to-tool mismatch, and experimental differential spectra from the measurement of the target 700. The target illustrated in FIG. 7 shows six adjustable model parameters: including a first thickness (T1) and a second thickness (T2) of different layers, a first critical dimension (CD1) and a second critical dimension (CD2) of overlaying lines, and a first sidewall angle (SWA1) and a second sidewall angle (SWA2) of the overlaying lines. Two wafers (wafer1 and wafer2) with the illustrated NFET application where measured in two different optical metrology tools (tool1 and tool2) of the same type, i.e., Atlas® II manufactured by Nanometrics, Inc. In each wafer 30 targets that are uniformly distributed on the surface of the wafer were measured. The Normal incidence reflectance spectra sR and pR (respectively "s" polarized and "p" polarized) as well as the ellipsometric NCS spectra were acquired for each of the 30 targets on each of wafer1 and wafer2 by tool1 and tool2.

The first column of FIG. 8 shows 30 superimposed spectra of the 30 targets on wafer 1 measured at tool1, with the horizontal axis representing wavelength in nanometers and the vertical axis representing spectra amplitude in arbitrary units. The second column in FIG. 8 illustrates the model bias for each type of acquired spectra. The model bias is the difference between the experimental spectra and the best fitted spectra determined using a conventional fitting process. The third column of FIG. 8 illustrates the differential experimental spectra, i.e., the difference between the experimental spectra and the anchor spectra, given by equation 6, where the first target (out of the 30 targets) on wafer1 was treated as the reference target sample to produce the anchor spectrum and the anchor parameters were obtained using a conventional fitting process of the anchor spectrum acquired in tool 1.

A theoretical model for the target 700 was developed using RCWA (rigorous coupled wave analysis) and the theoretical spectra, i.e., simulated spectra, were fitted to the experimental spectra by adjusting the six model parameters T1, T2, CD1, CD2, SWA1, and SWA2 illustrated in FIG. 7. The fittings were performed using the differential fitting approach discussed herein, where the first target (out of the 30 targets) on wafer1 was treated as the reference target sample to produce the anchor spectrum as well as the anchor parameters, which were determined by tool1. When performing the differential fitting at tool2, the anchor spectrum is the spectrum acquired by tool2 from the first target (out of the 30 targets) on wafer1. For the sake of comparison, a conventional fitting process, as described in equation 1, was also performed. For example, as discussed above, the second column of FIG. 8 the difference between the experimental spectra and the best fitted spectra determined using the conventional fitting process, i.e., the model bias.

FIG. 9 illustrates the average parameter mismatch between tool1 and tool2 for the two different wafers, wafer1 and wafer2 (identified in FIG. 9 as slot#1 and 2). In other words, FIG. 9 shows for each wafer (wafer1 and wafer 2), the average, along the 30 targets, of the absolute difference between the fittings obtained from tool1 spectra and tool2 spectra. Each of the six parameters identified with target 700 is shown in FIG. 9 as a separate bar graph, where the conventional fitting process is illustrated with a black bar, and the differential fitting process, as described herein, is illustrated with a gray bar. As can be seen in FIG. 9, the differential fitting approach introduces a significant improvement in the tool-to-tool matching.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method of measuring parameters of a sample with an optical metrology tool, the method comprising:

illuminating one or more reference samples with light from the optical metrology tool;

acquiring one or more spectrum from the light after interacting with the one or more reference samples using the optical metrology tool;

determining an anchor spectrum for the optical metrology tool using the one or more spectrum acquired from the one or more reference samples using the optical metrology tool, wherein the anchor spectrum is a reference spectrum that is used to generate differential experimental spectra for all samples measured with the optical metrology tool;

illuminating the sample with the light from the optical metrology tool;

acquiring a target spectrum from the light after interacting with the sample using the optical metrology tool;

generating a differential experimental spectrum based on a difference between the target spectrum and the anchor spectrum;

fitting the differential experimental spectrum to a differential simulated spectrum, wherein the differential simulated spectrum is based on a difference between a spectrum simulated using a model having variable parameters and a spectrum simulated using a model having anchor parameters, wherein the anchor parameters are determined for the one or more reference samples using one or more reference optical metrology tools; and determining the parameters for the sample based on the variable parameters in the differential simulated spectrum that is a best fit to the differential experimental spectrum.

2. The method of claim 1, wherein the one or more reference samples and the sample are associated with a same application, wherein the application defines one or more fabrication processes and process parameters.

3. The method of claim 1, wherein the anchor parameters for the one or more reference samples is a statistical combination of parameters determined for a plurality of reference samples.

4. The method of claim 1, wherein the anchor parameters for the one or more reference samples are determined using a statistical combination of spectra acquired for a plurality of reference samples.

5. The method of claim 1, wherein the anchor parameters for the one or more reference samples are determined based on a statistical combination of parameters determined for one or more reference samples using a plurality of reference optical metrology tools.

6. The method of claim 1, wherein the anchor parameters for the one or more reference samples are determined using a statistical combination of spectra acquired for the one or more reference samples using a plurality of reference optical metrology tools.

7. The method of claim 1, wherein the anchor spectrum and the target spectrum are functions of at least one of wavelength, angle of incidence, angle of azimuth or a combination of the foregoing.

8. The method of claim 1, wherein the anchor spectrum and the target spectrum are one of reflectance spectra, ellipsometric spectra, Mueller matrix spectra, Jones matrix spectra or Fourier coefficients spectra.

9. The method of claim 1, wherein fitting the differential experimental spectrum to the differential simulated spectrum comprises minimizing a cost function to find a best match.

10. The method of claim 1, wherein differential simulated spectra is stored in a library and fitting the differential experimental spectrum to the differential simulated spectrum comprises determining the differential simulated spectrum is a best match in the library for the differential experimental spectrum or interpolating the differential experimental spectrum based on entries in the library.

11. An optical metrology tool comprising:
an illumination source to produce illumination;
an optical system that focuses the illumination into incident light on a sample;
a detector that detects the illumination after being incident on the sample; and
a processor coupled to receive an output signal from the detector, wherein the processor is configured to cause the illumination source to illuminate one or more reference samples with light, acquire one or more spectrum from the light after interacting with the one or more reference samples from the output signal from the detector, determine an anchor spectrum using the one or more spectrum acquired from the one or more reference samples, wherein the anchor spectrum is a reference spectrum that is used to generate differential experimental spectra for all samples measured with the optical metrology tool, acquire a target spectrum from the light after interacting with the sample from the output signal from the detector, generate a differential experimental spectrum based on a difference between the target spectrum and the anchor spectrum, fit the differential experimental spectrum to a differential simulated spectrum, wherein the differential simulated spectrum is based on a difference between a spectrum simulated using a model having variable parameters and a spectrum simulated using a model having anchor parameters, wherein the anchor parameters are determined for the one or more reference samples using one or more reference optical metrology tools, and determine parameters for the sample based on the variable parameters in the differential simulated spectrum that is a best fit to the differential experimental spectrum.

12. The optical metrology tool of claim 11, wherein the one or more reference samples and the sample are associated with a same application, wherein the application defines one or more fabrication processes and process parameters.

13. The optical metrology tool of claim 11, wherein the anchor parameters for the one or more reference samples is a statistical combination of parameters determined for a plurality of reference samples.

14. The optical metrology tool of claim 11, wherein the anchor parameters for the one or more reference samples are determined using a statistical combination of spectra acquired for a plurality of reference samples.

15. The optical metrology tool of claim 11, wherein the anchor parameters for the one or more reference samples are determined based on a statistical combination of parameters determined for one or more reference samples using a plurality of reference optical metrology tools.

16. The optical metrology tool of claim 11, wherein the anchor parameters for the one or more reference samples are determined using a statistical combination of spectra acquired for the one or more reference samples using a plurality of reference optical metrology tools.

17. The optical metrology tool of claim 11, wherein the anchor spectrum and the target spectrum are functions of at least one of wavelength, angle of incidence, angle of azimuth or a combination of the foregoing.

18. The optical metrology tool of claim 11, wherein the anchor spectrum and the target spectrum are one of reflectance spectra, ellipsometric spectra, Mueller matrix spectra, Jones matrix spectra or Fourier coefficients spectra.

19. The optical metrology tool of claim 11, wherein the processor is configured to fit the differential experimental spectrum to the differential simulated spectrum by being configured to minimize a cost function to find the best fit.

20. The optical metrology tool of claim 11, wherein differential simulated spectra is stored in a library and wherein the processor is configured to fit the differential experimental spectrum to the differential simulated spectrum by being configured to determine the differential simulated spectrum is the best fit in the library for the differential experimental spectrum or interpolate the differential experimental spectrum based on entries in the library.

21. The method of claim 1, wherein the anchor parameters are used with a plurality of optical metrology tools, wherein the anchor spectrum for the one or more reference samples obtained using the optical metrology tool is different from anchor spectra acquired by each optical metrology tool in the plurality of optical metrology tools.

22. The method of claim 21, wherein each optical metrology tool in the plurality of optical metrology tools acquires a different anchor spectrum for the one or more reference samples.

* * * * *